United States Patent
Kim et al.

(10) Patent No.: US 10,882,533 B2
(45) Date of Patent: Jan. 5, 2021

(54) DROWSY DRIVING MANAGEMENT DEVICE, SYSTEM INCLUDING THE SAME, AND METHOD THEREOF

(71) Applicants: HYUNDAI MOTOR COMPANY, Seoul (KR); KIA MOTORS CORPORATION, Seoul (KR)

(72) Inventors: Jin Kwon Kim, Suwon-si (KR); Byoung Joon Lee, Suwon-si (KR); Sam Yong Kim, Hwaseong-si (KR)

(73) Assignees: HYUNDAI MOTOR COMPANY, Seoul (KR); KIA MOTORS CORPORATION, Seoul (KR)

(*) Notice: Subject to any disclaimer, the term of this patent is extended or adjusted under 35 U.S.C. 154(b) by 0 days.

(21) Appl. No.: 16/668,613

(22) Filed: Oct. 30, 2019

(65) Prior Publication Data
US 2020/0317208 A1 Oct. 8, 2020

(30) Foreign Application Priority Data
Apr. 3, 2019 (KR) .................. 10-2019-0039170

(51) Int. Cl.
| | |
|---|---|
| B60W 40/08 | (2012.01) |
| G08B 21/06 | (2006.01) |
| G06K 9/00 | (2006.01) |
| A61B 3/113 | (2006.01) |
| B60W 50/16 | (2020.01) |
| B60W 40/114 | (2012.01) |
| A61B 5/00 | (2006.01) |
| B60W 40/107 | (2012.01) |
| B60W 50/14 | (2020.01) |

(52) U.S. Cl.
CPC ............ *B60W 40/08* (2013.01); *A61B 3/113* (2013.01); *A61B 5/4809* (2013.01); *B60W 40/114* (2013.01); *B60W 50/16* (2013.01); *G06K 9/00845* (2013.01); *G08B 21/06* (2013.01); *B60W 40/107* (2013.01); *B60W 2040/0827* (2013.01); *B60W 2050/143* (2013.01)

(58) Field of Classification Search
CPC ..................................................... B60W 40/09
See application file for complete search history.

(56) References Cited

U.S. PATENT DOCUMENTS

| | | | |
|---|---|---|---|
| 6,091,334 A | 7/2000 | Galiana et al. | |
| 7,071,831 B2 | 7/2006 | Johns | |
| 9,008,857 B2 | 4/2015 | Kim et al. | |
| 2004/0233061 A1 | 11/2004 | Johns | |

(Continued)

FOREIGN PATENT DOCUMENTS

WO 03/039358 A1 5/2013

*Primary Examiner* — Nabil H Syed
*Assistant Examiner* — Cal J Eustaquio
(74) *Attorney, Agent, or Firm* — Morgan, Lewis & Bockius LLP

(57) ABSTRACT

A drowsy driving management device includes: a processor configured to determine whether slow eye movement of a user occurs and whether there is no change in steering torque and to determine that the user drives while drowsy when the slow eye movement of the user occurs and when there is no change in the steering torque for a predetermined period of time; and a storage that stores information indicating whether the slow eye movement occurs and a result of determining whether there is no change in the steering torque.

16 Claims, 7 Drawing Sheets

(56) References Cited

U.S. PATENT DOCUMENTS

| | | | |
|---|---|---|---|
| 2006/0202841 A1 | 9/2006 | Johns | |
| 2007/0121066 A1* | 5/2007 | Nashner | A61B 3/028 351/210 |
| 2008/0243558 A1* | 10/2008 | Gupte | G06Q 40/08 705/4 |
| 2010/0033333 A1* | 2/2010 | Victor | A61B 5/1114 340/576 |
| 2016/0052524 A1* | 2/2016 | Kim | G08B 21/06 340/576 |
| 2017/0080856 A1* | 3/2017 | Enomoto | A61B 5/18 |

* cited by examiner

DROWSY DRIVING MANAGEMENT DEVICE, SYSTEM INCLUDING THE SAME, AND METHOD THEREOF

CROSS-REFERENCE TO RELATED APPLICATION

This application is claims the benefit of priority to Korean Patent Application No. 10-2019-0039170, filed in the Korean Intellectual Property Office on Apr. 3, 2019, the entire contents of which are incorporated herein by reference.

TECHNICAL FIELD

The present disclosure relates to a drowsy driving management device, a system including the same, and a method thereof, and more particularly, relates to technologies of early and accurately determining drowsy driving based on slow eye movement and a vehicle signal.

BACKGROUND

A drowsy driving warning function of determining whether a user drives while drowsy in connection with a vehicle service and warning the user of the drowsy driving has been expanded and applied.

Such drowsy driving warning function has the accuracy of determining drowsy driving and a time when a warning occurs as important performance indexes. Particularly, the time when the warning occurs has high availability only when a warning should occur when the user falls into a sleep (at the sleep-onset), but currently commercialized technologies do not satisfy it.

The currently mass-produced drowsy driving warning function is roughly divided into two manners including an indirect manner of analyzing a driving pattern and determining drowsy driving and a direct manner of determining drowsy driving based on an eye opening/closing image of a driver.

Because the indirect manner based on the driving pattern has low accuracy and a high difference between a warning time and a sleep-onset, there is reduced availability. On the other hand, in technologies of determining drowsy driving based on an eye opening/closing image of the driver, which is the direct manner, there is high accuracy because a warning occurs by detecting long eye closing, however, when a driver shows eye closing on a rear road for a relatively long period of time, a danger level may be high. Therefore, there is a need for accurately determining whether the driver drives while drowsy at the beginning of drowsiness and warning the driver of the drowsy driving.

SUMMARY

The present disclosure has been made to solve the above-mentioned problems occurring in the prior art while advantages achieved by the prior art are maintained intact.

An aspect of the present disclosure provides a drowsy driving management device for early and accurately detecting drowsy driving of a user based on slow eye movement and an interval where there is no change in steering torque by a vehicle signal, a system including the same, and a method thereof.

The technical problems to be solved by the present inventive concept are not limited to the aforementioned problems, and any other technical problems not mentioned herein will be clearly understood from the following description by those skilled in the art to which the present disclosure pertains.

According to an exemplary embodiment of the present disclosure, a drowsy driving management device may include: a processor configured to determine whether slow eye movement of a user occurs and whether there is no change in steering torque and to determine that the user drives while drowsy when the slow eye movement of the user occurs and when there is no change in the steering torque for a predetermined period of time; and a storage that stores information indicating whether the slow eye movement occurs and a result of determining whether there is no change in the steering torque.

The processor may determine that the driver drives while drowsy, when there is no user maneuver in the state where the slow eye movement of the user occurs and where there is no change in the steering torque during the predetermined period of time.

The processor may calculate eye movement information with respect to a vehicle based on information about a fixation of the user and information about a head pose of the user based on image data and may calculate eye movement information with respect to an external environment based on the eye movement information with respect to the vehicle.

The information about the fixation may include a gaze yaw angle and a gaze pitch angle. The information about the head pose may include a head pose yaw angle and a head pose pitch angle.

The processor may calculate an eye movement yaw angle with respect to the vehicle in the eye movement information with respect to the vehicle by subtracting the head pose yaw angle from the gaze yaw angle and may calculate an eye movement pitch angle with respect to the vehicle in the eye movement information with respect to the vehicle by subtracting the head pose pitch angle from the gaze pitch angle.

The processor may calculate an eye movement yaw angle with respect to the external environment in the eye movement information with respect to the external environment using the eye movement yaw angle with respect to the vehicle and a vehicle yaw rate and may calculate an eye movement pitch angle with respect to the external environment in the eye movement information with respect to the external environment using the eye movement pitch angle with respect to the vehicle and a vehicle pitch angle.

The processor may calculate an eye movement distance during the predetermined period of time using a value obtained by adding the eye movement yaw angle with respect to the external environment and the eye movement pitch angle with respect to the external environment and may determine that the slow eye movement occurs, when the eye movement distance is less than a predetermined reference value.

The processor may determine that there is no change in the steering torque, when an output value of a steering torque sensor is less than a predetermined reference value.

According to another exemplary embodiment of the present disclosure, a vehicle system may include: a drowsy driving management device configured to determine whether slow eye movement of a user occurs and whether there is no change in steering torque and to determine that the user drives while drowsy when the slow eye movement of the user occurs and when there is no change in the steering torque for a predetermined period of time and a warning device that outputs a warning to the user, when it is determined that the user drives while drowsy.

The warning device may provide at least one or more of a visual warning, a tactile warning, and an audible warning.

The vehicle system may further include a camera that detects information about a gaze of the user and information about a head pose of the user, a yaw pitch sensor that senses a vehicle yaw rate and a vehicle pitch angle, a steering torque sensor that senses a change in steering torque of a vehicle, and a decelerator/accelerator pedal sensor that senses a change value in decelerator/accelerator pedal.

The drowsy driving management device may include a processor that determines whether the slow eye movement of the user occurs and whether there is no change in the steering torque and determines that the user drives while drowsy when the slow eye movement of the user occurs and when there is no change in the steering torque during the predetermined period of time and a storage that stores information indicating whether the slow eye movement occurs and the result of determining whether there is no change in the steering torque, the information and the result being obtained by the processor.

The processor may determine that the driver drives while drowsy, when there is no user maneuver in the state where the slow eye movement of the user occurs and where there is no change in the steering torque during the predetermined period of time.

According to another exemplary embodiment of the present disclosure, a drowsy driving management method may include: determining whether slow eye movement of a user occurs and whether there is no change in steering torque; and determining that the user drives while drowsy, when the slow eye movement of the user occurs and when there is no change in the steering torque for a predetermined period of time.

The determining that the user drives while drowsy may include determining that the driver drives while drowsy, when there is no user maneuver in the state where the slow eye movement of the user occurs and where there is no change in the steering torque during the predetermined period of time.

The determining whether the slow eye movement of the user occurs and whether there is no change in the steering torque may include calculating eye movement information with respect to a vehicle based on information about a fixation of the user and information about a head pose of the user based on image data and calculating eye movement information with respect to an external environment based on the eye movement information with respect to the vehicle.

The information about the fixation may include a gaze yaw angle and a gaze pitch angle. The information about the head pose may include a head pose yaw angle and a head pose pitch angle.

The determining whether the slow eye movement of the user occurs and whether there is no change in the steering torque may include calculating an eye movement yaw angle with respect to the vehicle in the eye movement information with respect to the vehicle by subtracting the head pose yaw angle from the gaze yaw angle and calculating an eye movement pitch angle with respect to the vehicle in the eye movement information with respect to the vehicle by subtracting the head pose pitch angle from the gaze pitch angle.

The determining whether the slow eye movement of the user occurs and whether there is no change in the steering torque may include calculating an eye movement yaw angle with respect to the external environment in the eye movement information with respect to the external environment using the eye movement yaw angle with respect to the vehicle and a vehicle yaw rate and calculating an eye movement pitch angle with respect to the external environment in the eye movement information with respect to the external environment using the eye movement pitch angle with respect to the vehicle and a vehicle pitch angle.

The determining whether the slow eye movement of the user occurs and whether there is no change in the steering torque may include calculating an eye movement distance during the predetermined period of time using a value obtained by adding the eye movement yaw angle with respect to the external environment and the eye movement pitch angle with respect to the external environment and determining that the slow eye movement occurs, when the eye movement distance is less than a predetermined reference value.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
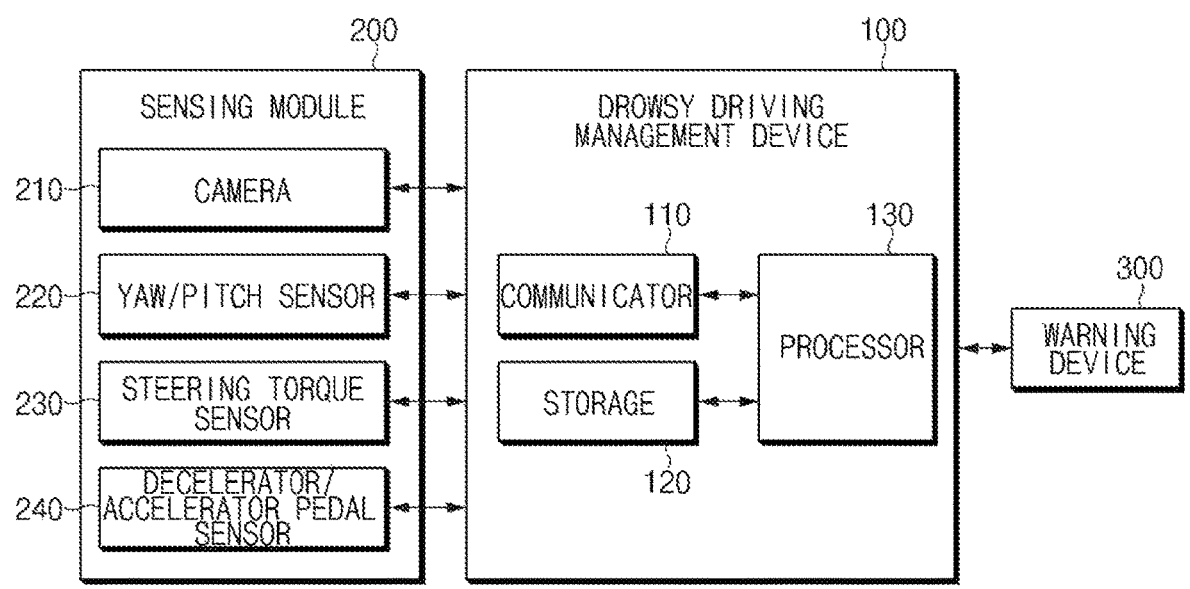
FIG. 1 is a block diagram illustrating a configuration of a vehicle system including a drowsy driving management device according to an exemplary embodiment of the present disclosure.

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of well-known features or functions will be ruled out in order not to unnecessarily obscure the gist of the present disclosure.

In describing the components of the embodiment according to the present disclosure, terms such as first, second, "A", "B", (a), (b), and the like may be used. These terms are merely intended to distinguish one component from another component, and the terms do not limit the nature, sequence or order of the constituent components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

Because drowsiness relaxes muscles, it is difficult to take purposeful action such as driving. In case of eyes, when drowsy, the movement of pupils is not indicated as saccade and the fixation of the eyes moves at a slow speed. In case of hands, in a drowsy situation, a clear behavior is not performed due to muscle relaxation and the strength of grasp of the hands is reduced. Thus, an exemplary embodiment of the present disclosure may disclose technologies of determining drowsy driving at the beginning of drowsiness based on slow eye movement of a user and a vehicle signal (e.g., a steering torque and information indicating whether various switches are manipulated) and warning the user to prevent accident by the drowsy driving.

Hereinafter, a description will be given in detail of embodiments of the prevent disclosure with reference to FIGS. 1 and 7.

FIG. 1 is a block diagram illustrating a configuration of a vehicle system including a drowsy driving management device according to an exemplary embodiment of the present disclosure.

Referring to FIG. 1, the vehicle system according to an exemplary embodiment of the present disclosure may include a drowsy driving management device 100, a sensing module 200, and a warning device 300.

The drowsy driving management device 100 may determine whether slow eye movement of a user occurs and whether there is no change in steering torque. When the slow eye movement of the user occurs and when there is no change in steering torque for a predetermined period of time, the drowsy driving management device 100 may determine that the user drives while drowsy.

Furthermore, when there is no user maneuver in the state where the slow eye movement of the user occurs and where there is no change in the steering torque for the predetermined period of time, the drowsy driving management device 100 may determine that the user drives while drowsy.

The drowsy driving management device 100 may include a communicator 110, a storage 120, and a processor 130.

The communicator 110 may be a hardware device implemented with various electronic circuits to transmit and receive a signal over a wireless or wired connection. In an embodiment of the present disclosure, the communicator 110 may perform inter-vehicle communication through controller area network (CAN) communication, local interconnect network (LIN) communication, or the like and may communicate with the sensing module 200 and the warning device 300.

The storage 120 may store a sensing result of the sensing module 200 and information indicating whether slow eye movement occurs, the result of determining whether there is no change in steering torque, and the like, obtained by the processor 130. The storage 120 may include at least one type of storage medium, such as a flash memory type memory, a hard disk type memory, a micro type memory, a card type memory (e.g., a secure digital (SD) card or an extreme digital (XD) card), a random access memory (RAM), a static RAM (SRAM), a read-only memory (ROM), a programmable ROM (PROM), an electrically erasable PROM (EEPROM), a magnetic RAM (MRAM), a magnetic disk, and an optical disk.

The processor 130 may be electrically connected with the communicator 110, the storage 120, the warning device 300, or the like and may electrically control the respective components. The processor 130 may be an electrical circuit which executes instructions of software and may perform a variety of data processing and calculation described below.

The processor 130 may determine whether slow eye movement of the user occurs and whether there is no change in steering torque. When the slow eye movement of the user occurs and when there is no change in the steering torque during a predetermined time, the processor 130 may determine that the user drives while drowsy.

When there is no user maneuver in the state when the slow eye movement of the user occurs and when there is no change in the steering torque for the predetermined period of time, the processor 130 may determine that the user drives while drowsy.

The processor 130 may calculate eye movement information with respect to a vehicle based on information about a fixation of the user and information about a head pose of the user based on image data and may calculate eye movement information with respect to an external environment based on the eye movement information with respect to the vehicle.

The processor 130 may subtracts a head pose yaw angle from a gaze yaw angle to calculate an eye movement yaw angle with respect to the vehicle in the eye movement information with respect to the vehicle. The processor 130 may subtract a head pose pitch angle from a gaze pitch angle to calculate an eye movement pitch angle with respect to the vehicle in the eye movement information with respect to the vehicle.

The processor 130 may calculate an eye movement yaw angle with respect to the external environment in the eye movement information with respect to the external environment using the eye movement yaw angle with respect to the vehicle and a vehicle yaw rate. The processor 130 may calculate an eye movement pitch angle with respect to the external environment in the eye movement information with respect to the external environment using the eye movement pitch angle with respect to the vehicle and a vehicle pitch angle.

The processor 130 may calculate an eye movement distance during a predetermined period of time using a value obtained by adding the eye movement yaw angle with respect to the external environment and the eye movement pitch angle with respect to the external environment. When the eye movement distance is less than a predetermined reference value, the processor 130 may determine that the slow eye movement occurs.

When an output value of a steering torque sensor 230 is less than a predetermined reference value, the processor 130 may determine that there is no change in steering torque.

The sensing module 200 may sense information about a fixation of the user, information about a head pose (head movement) of the user, a vehicle yaw rate, a vehicle pitch angle, a change in steering torque of the vehicle, whether a decelerator/accelerator pedal operates, or the like.

To this end, the sensing module 200 may include a camera 210, a yaw/pitch sensor 220, the steering torque sensor 230, and a decelerator/accelerator pedal sensor 240.

The camera 210 may be driver status monitoring (DSM) and may detect information about a gaze of the user and information about a head pose of the user.

The yaw/pitch sensor 220 may sense a vehicle yaw rate and a vehicle pitch angle and may deliver the sensed information to the drowsy driving management device 100.

The steering torque sensor 230 may sense a change in the steering torque of the vehicle and may deliver the sensed information to the drowsy driving management device 100.

The decelerator/accelerator pedal sensor 240 may sense a change value in decelerator/accelerator pedal and may deliver the sensed information to the drowsy driving management device 100.

Although not illustrated in FIG. 1, the vehicle system may further include various switches capable of being manipulated by the user.

When it is determined that the user drives while drowsy by the drowsy driving management device 100, the warning device 300 may be controlled by the drowsy driving management device 100 to output at least one or more of a visual warning, a tactile warning, and an audible warning to the user and to guide the user to shake off sleepiness to display a screen of recommending the user to take a break, recommending the user to operate a driving assistance function, or guiding the user toward a rest area or a sleeping shelter or outputting a voice to the user. The warning device 300 may be implemented as a head-up display (HUD), a cluster, an audio video navigation (AVN), or the like. Furthermore, the warning device 300 may include at least one of a liquid crystal display (LCD), a thin film transistor-LCD (TFT-LCD), a light emitting diode (LED) display, an organic LED (OLED) display, an active matrix OLED (AMOLED) display, a flexible display, a bended display, and a three-dimensional (3D) display. Some thereof may be implemented as transparent displays configured as a transparent type or a semi-transparent type to see the outside. Moreover, the warning device 300 may be implemented as a touchscreen including a touch panel to be used as an input device other than an output device.

As such, an embodiment of the present disclosure may determine drowsy driving of the user with high reliability at the beginning of the drowsy driving based on slow eye movement and an interval where there is no change in steering torque. Furthermore, when there are no inputs for manipulating various switches, such as a pedal operation, from the user as well as the slow eye movement and the interval where there is no change in the steering torque, an embodiment of the present disclosure may determine that the driver drives while drowsy.

Figure 2:
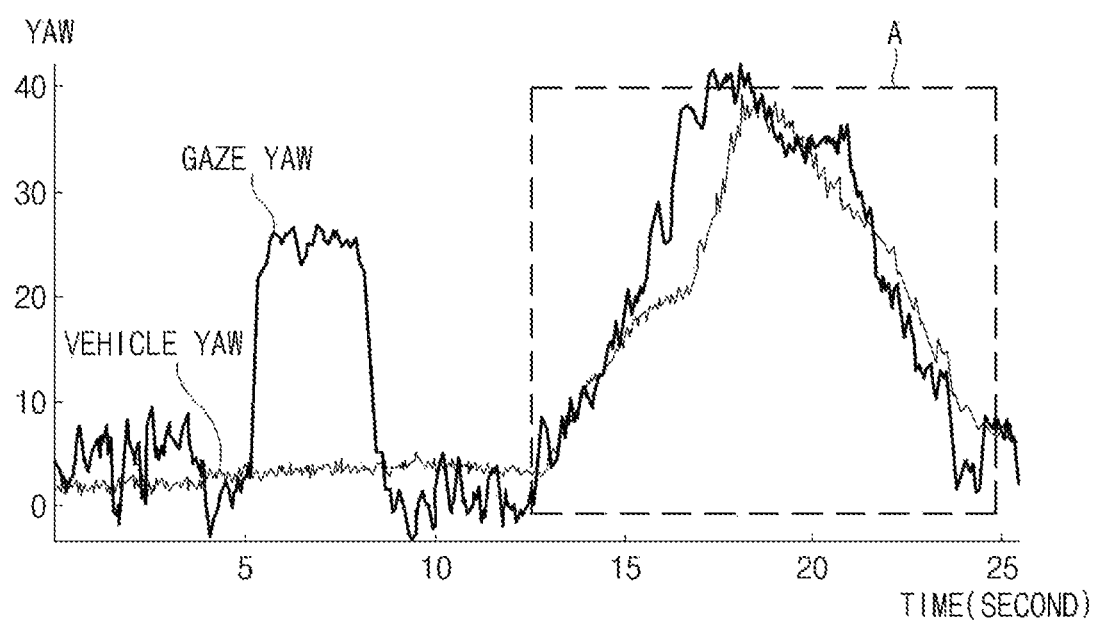
FIG. 2 is a graph illustrating a gaze yaw and a vehicle yaw according to an exemplary embodiment of the present disclosure.

FIG. 2 is a graph illustrating a gaze yaw and a vehicle yaw according to an exemplary embodiment of the present disclosure. Referring to FIG. 2, when the vehicle moves while a user looks at one point outside a vehicle, because it is shown that a fixation with respect to the inside of the vehicle moves slowly, it may be incorrectly detected as slow eye movement.

Figure 3:
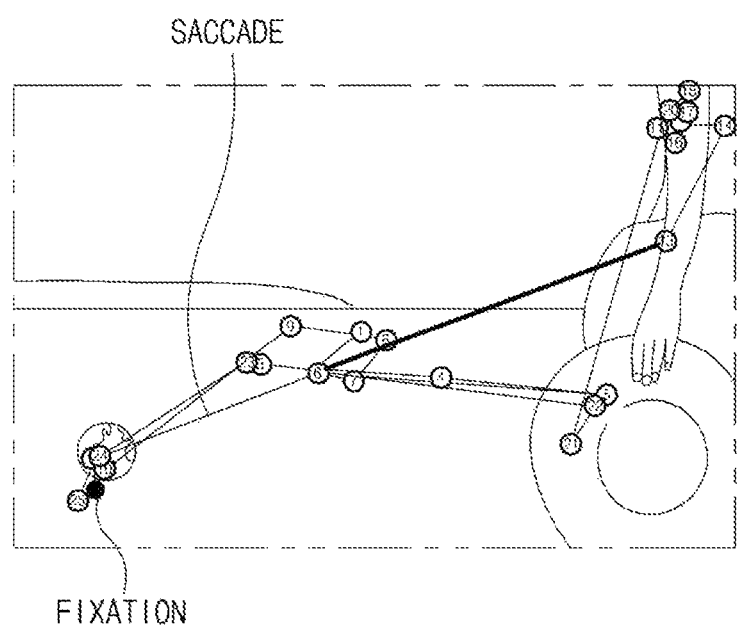
FIG. 3 is a drawing illustrating an exemplary operation of fixation and saccade according to an exemplary embodiment of the present disclosure.
Figure 4:
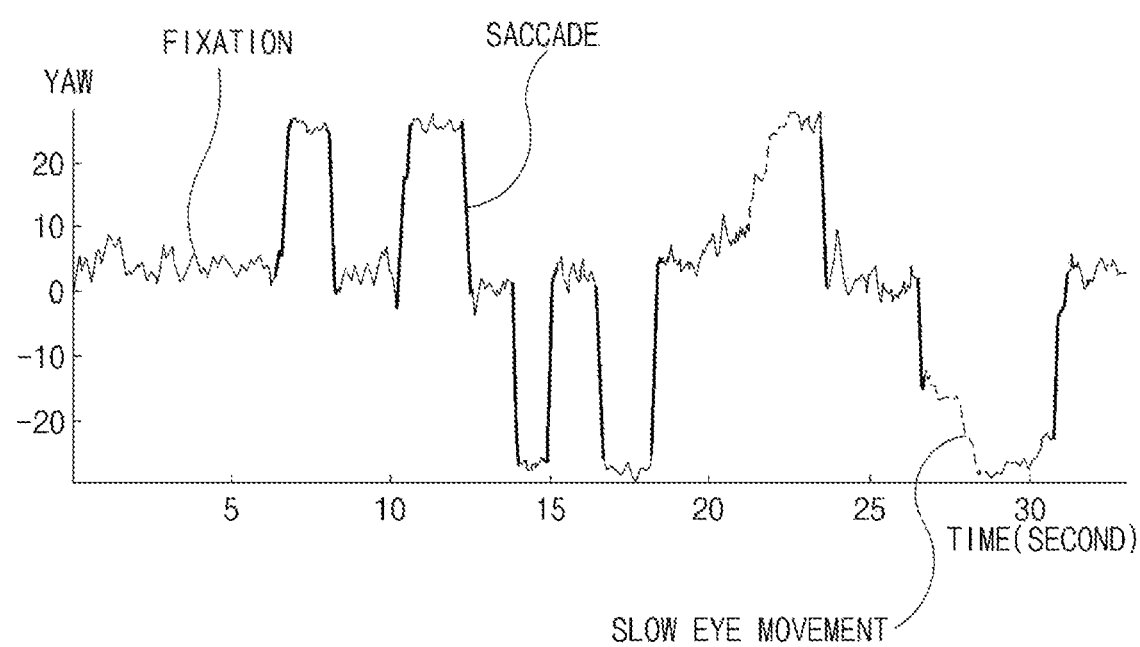
FIG. 4 is a drawing illustrating a gaze yaw indicated by fixation, saccade, and slow eye movement according to an exemplary embodiment of the present disclosure.

FIG. 3 is a drawing illustrating an exemplary operation of fixation and saccade according to an exemplary embodiment of the present disclosure. FIG. 4 is a drawing illustrating a gaze yaw indicated by fixation, saccade, and slow eye movement according to an exemplary embodiment of the present disclosure.

Referring to FIG. 3, when a user who in a normal state rather than a drowsy state wants to see another place while looking at one place, he or she may perform eye movement in the form of quickly moving his or her fixation and looking at another point. Such eye movement is called saccade. When the eye movement is measured using a gaze tracking camera, it is shown in FIG. 3. On the other hand, when the user feels drowsy or is cognitively careless, slow eye movement rather than saccade is shown. In other words, the slow eye movement refers to a phenomenon in which a fixation flows without saccade between a fixation and a fixation, and it is shown in FIG. 4.

Referring to FIG. 4, when a fixation the user looks at is moved to another fixation, saccade in a straight form is shown. When the user is in a drowsy state, it may be seen that a slow eye movement state which is a state where the straight form is in disorder is shown.

Figure 5:
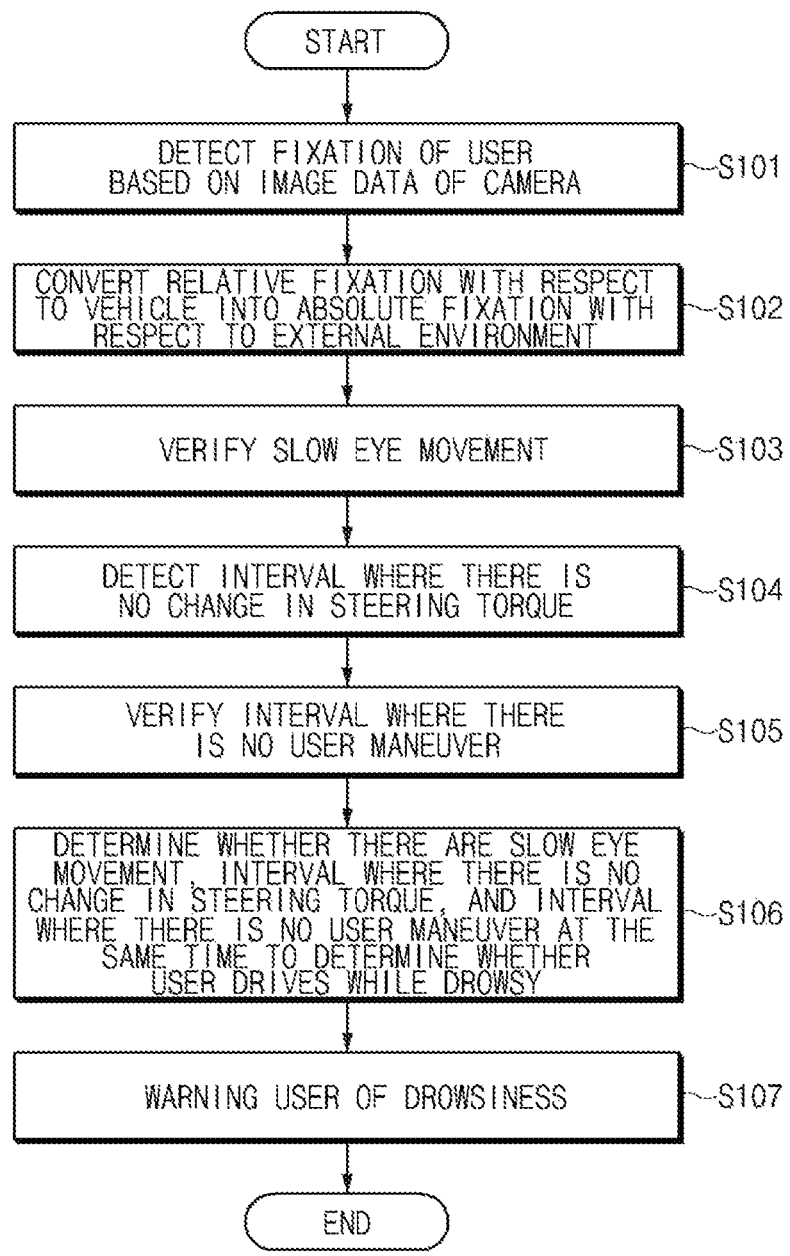
FIG. 5 is a flowchart illustrating a drowsy driving management method according to an exemplary embodiment of the present disclosure.

Hereinafter, a description will be given in detail of a drowsy driving management method according to an embodiment of the present disclosure with reference to FIG. 5. FIG. 5 is a flowchart illustrating a drowsy driving management method according to an embodiment of the present disclosure.

Hereinafter, it is assumed that a drowsy driving management device 100 of FIG. 1 performs a process of FIG. 5. Furthermore, in a description of FIG. 5, an operation described as being performed by an apparatus may be understood as being controlled by a processor 130 of the drowsy driving management device 100.

Referring to FIG. 5, in S101, the drowsy driving management device 100 may detect a fixation which is a point a user looks at, based on image data of a camera 210 of FIG. 1. In this case, because the fixation moves by adding eye movement and head movement, the drowsy driving management device 100 may subtract a fixation due to the head movement from the fixation to output only a fixation due to the eye movement.

In S102, the drowsy driving management device 100 may convert a relative fixation with respect to a vehicle into an absolute fixation with respect to an external environment using the fixation and a value output from a yaw/pitch sensor 220 of FIG. 1. In other words, because the camera 210 is mounted on the vehicle, a fixation measured using the camera 210 may be a relative position with respect to the vehicle. However, the fixation may differ from general slow eye movement in the moving vehicle. For example, when the vehicle moves while the user looks at one point outside the vehicle, because it is shown that a fixation with reference to the inside of the vehicle moves slowly, the fixation may be incorrectly detected as slow eye movement. To prevent such a phenomenon, the drowsy driving management device 100 may calculate a fixation compensating movement of the vehicle to detect the slow eye movement. The drowsy driving management device 100 may convert the relative fixation with respect to the vehicle into the absolute fixation with respect to the external environment.

In S103, the drowsy driving management device 100 may verify the slow eye movement based on the fixation. When a person who in a normal state wants to see another place while looking at one place, he or she performs eye movement in the form of quickly moving a fixation and looking at another point. Such eye movement is called saccade. When the eye movement is measured using a gaze tracking camera, it is shown in FIG. 3. On the other hand, the user feels drowsy or is cognitively careless, slow eye movement is shown. The slow eye movement refers to a phenomenon in which a fixation flows without saccade between a fixation and a fixation, and it is shown in FIG. 4.

In S104, the drowsy driving management device 100 may detect an interval where there is no change in steering torque, using a value output from the steering torque sensor 230 of FIG. 1. The drowsy driving management device 100 may determine whether there is no user maneuver for a decelerator/accelerator pedal and other buttons at a time such as the slow eye movement and the interval where there is no change in the steering torque to enhance the reliability of the detection.

In S105, the drowsy driving management device 100 may verify an interval where there is no user maneuver, based on an output value applied from a decelerator/accelerator pedal sensor 240 of FIG. 1 and a switch (not shown).

In S106, the drowsy driving management device 100 may determine whether there are the slow eye movement, the interval where there is no change in the steering torque, and the interval where there is no user maneuver at the same time to determine whether the user drives while drowsy.

When it is determined that the user drives while drowsy, in S107, the drowsy driving management device 100 may warn the user of drowsiness by a warning device 300 of FIG. 1.

Figure 6:
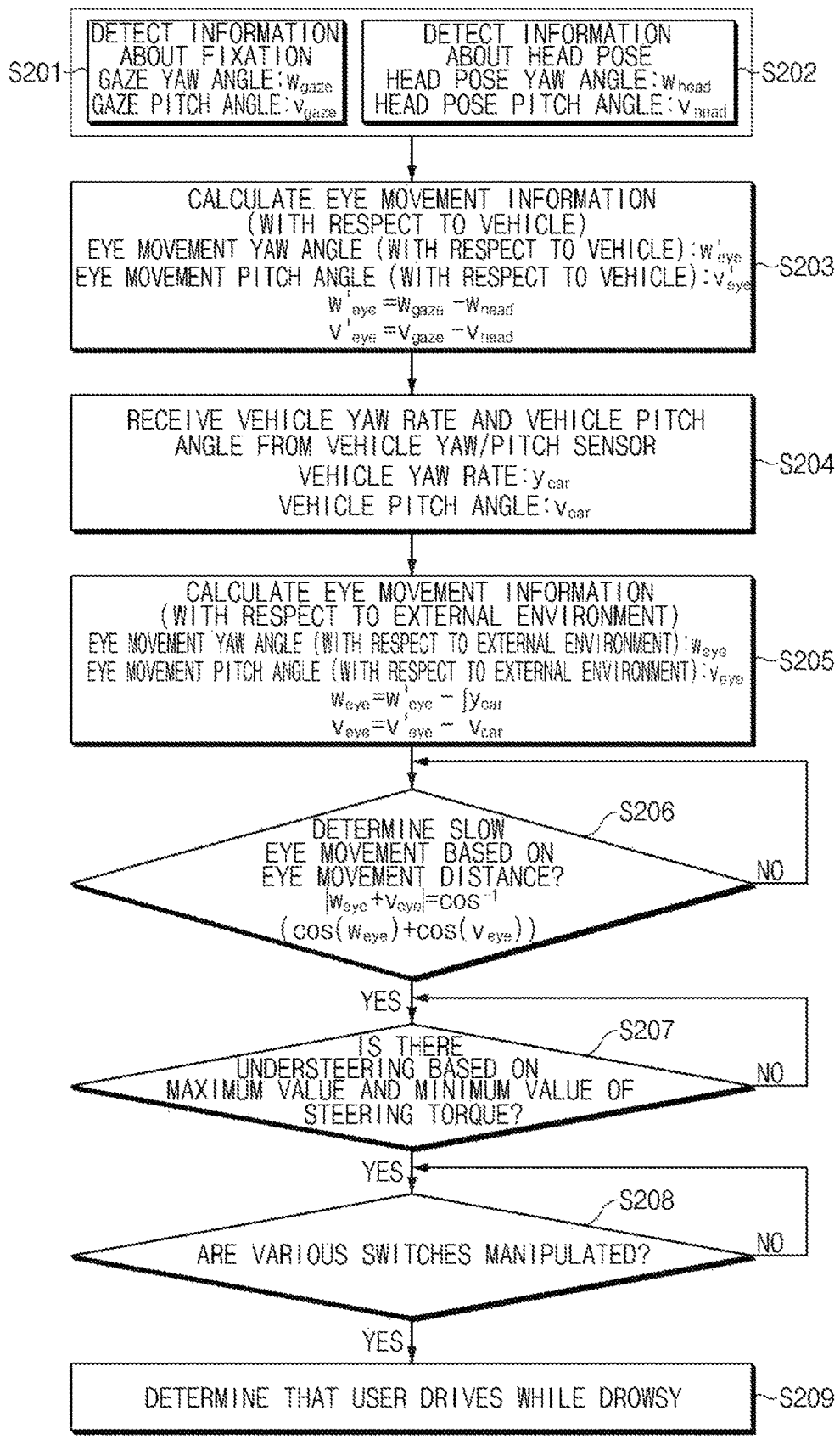
FIG. 6 is a detailed flowchart illustrating an example of calculating eye movement according to an exemplary embodiment of the present disclosure.

FIG. 6 is a detailed flowchart illustrating an example of calculating eye movement according to an exemplary embodiment of the present disclosure.

Referring to FIG. 6, in S201, a drowsy driving management device 100 of FIG. 1 may detect information about a fixation of a user from image data of a camera 210 of FIG. 1. In S202, the drowsy driving management device 100 may detect information about a head pose of the user.

In this case, the information about the fixation of the user may include a gaze yaw angle $w_{gaze}$ and a gaze pitch angle $v_{gaze}$. The information about the head pose may include a head pose yaw angle $w_{head}$ and a head pose pitch angle $v_{head}$.

In S203, the drowsy driving management device 100 may calculate eye movement information with respect to a vehicle using the information about the fixation of the user and the information about the head pose of the user.

In this case, the eye movement information with respect to the vehicle may include an eye movement yaw angle $w'_{eye}$ with respect to the vehicle and an eye movement pitch angle $v'_{eye}$ with respect to the vehicle.

In this case, the eye movement yaw angle $w'_{eye}$ with respect to the vehicle and the eye movement pitch angle $v'_{eye}$ with respect to the vehicle may be calculated as Equation 1 below.

$$w'_{eye} = w_{gaze} - w_{head}$$

$$v'_{eye} = v_{gaze} - v_{head} \qquad \text{[Equation 1]}$$

In other words, the drowsy driving management device 100 may subtract the head pose yaw angle $w_{head}$ from the gaze yaw angle $w_{gaze}$ to calculate the eye movement yaw angle $w'_{eye}$ with respect to the vehicle. The drowsy driving management device 100 may subtract the head pose pitch angle $v_{head}$ from the gaze pitch angle $v_{gaze}$ to calculate the eye movement pitch angle $v'_{eye}$ with respect to the vehicle.

After an amount of movement of the gaze yaw angle $w_{gaze}$ and the gaze pitch angle $v_{gaze}$ occurs greater than or equal to a certain rate (e.g., 30%) due to a head pose, the drowsy driving management device 100 may fail to determine drowsy driving. This is, when the user moves his or her gaze while turning his or her face (head), because it is not drowsy driving.

In S204, the drowsy driving management device 100 may receive a vehicle yaw rate $y_{ear}$ and a vehicle pitch angle $v_{car}$ from a yaw/pitch sensor 220 of FIG. 1.

In S205, the drowsy driving management device 100 may calculate eye movement information with respect to an external environment like Equation 2 below using the eye movement information with respect to the vehicle, the vehicle yaw rate $y_{car}$, and the vehicle pitch angle $v_{car}$ to convert a relative fixation with respect to the vehicle and an absolute fixation with respect to the external environment. In this case, the eye movement information with respect to the external environment may include an eye movement yaw angle $w_{eye}$ with respect to the external environment and an eye movement pitch angle $v_{eye}$ with respect to the external environment.

$$w_{eye} = w'_{eye} - \int y_{car}$$

$$v_{eye} = v'_{eye} - v_{car} \qquad \text{[Equation 2]}$$

In other words, the drowsy driving management device 100 may subtract an integral value in a period (e.g., 2 seconds) when the vehicle yaw rate $y_{car}$ is evaluated from the eye movement yaw angle $w'_{eye}$ with respect to the vehicle to calculate the eye movement yaw angle $w_{eye}$ with respect to the external environment. The drowsy driving management device 100 may subtract the vehicle pitch angle $v_{car}$ from the eye movement pitch angle $v'_{eye}$ with respect to the vehicle to calculate the eye movement pitch angle $v_{eye}$ with respect to the external environment.

In S206, the drowsy driving management device 100 may determine slow eye movement based on the total eye movement distance.

In other words, the drowsy driving management device 100 may determine whether an absolute value of a value obtained by adding the eye movement yaw angle $w_{eye}$ with respect to the external environment and the eye movement pitch angle $v_{eye}$ with respect to the external environment is identical to a value obtained by applying the sum of the eye movement yaw angle $w_{eye}$ with respect to the external environment and the eye movement pitch angle $v_{eye}$ with respect to the external environment, to which a cosine function is applied, to an arccosine function. When the absolute value is identical to the value, the drowsy driving management device 100 may determine that the slow eye movement occurs.

$$|w_{eye} + v_{eye}| = \cos^{-1}(\cos(w_{eye}) + \cos(v_{eye})) \qquad \text{[Equation 3]}$$

For example, when an eye movement distance for 2 seconds is greater than or equal to 10 degrees and when there is no eye movement at a speed of greater than or equal to 300 degrees/seconds within 2 seconds, the drowsy driving management device 100 may determine that the slow eye movement occurs. When a fixation moves by eye movement at a speed of greater than or equal to 300 degrees/seconds, the drowsy driving management device 100 may determine that saccade occurs.

In S207, the drowsy driving management device 100 may determine whether there is understeering, based on a maximum value and a minimum value of a steering torque. In other words, the drowsy driving management device 100 may determine whether an output value of a steering torque sensor 230 of FIG. 1 is kept small to detect an interval whether there is no change in steering torque due to reduction of the strength of grasp of the user. For example, when a value obtained by subtracting the minimum value of the steering torque from the maximum value of the steering torque within 2 seconds is less than 0.2 Nm and when a maximum value of an absolute value of the steering torque within 2 seconds is less than 0.4 Nm, the drowsy driving management device 100 may determine a current state as an understeering state (an interval where there is no steering torque).

In S208, the drowsy driving management device 100 may determine whether a turn signal operates, whether there is a change in decelerator/accelerator pedal, or whether various switches operate. For example, when there is a change greater than or equal to an accelerator pedal compression of 5% and when there is a change greater than or equal to a decelerator pedal compression of 10 bar, the drowsy driving management device 100 may determine that there is a change in a switch operation by the user.

When slow eye movement occurs, when in an understeering state, and when there is no operation of a turn signal, when there is no change in decelerator/accelerator pedal, and when there is no operations of various switches, in S209, the drowsy driving management device 100 may determine that the user drives while drowsy.

As such, an exemplary embodiment of the present disclosure may determine drowsy driving of the user with higher reliability than long eye opening and closing which is an existing drowsy driving detection method, based on slow eye movement and muscle relaxation which are an initial drowsy biomarker and may provide a warning at a quick, accurate time.

Furthermore, when determining slow eye movement and saccade using a camera of monitoring a user's face, an embodiment of the present disclosure may compensate a yaw and pitch of the vehicle to prevent similar slow eye movement by vehicle motion from being incorrectly detected, thus more accurately detecting drowsy driving.

Figure 7:
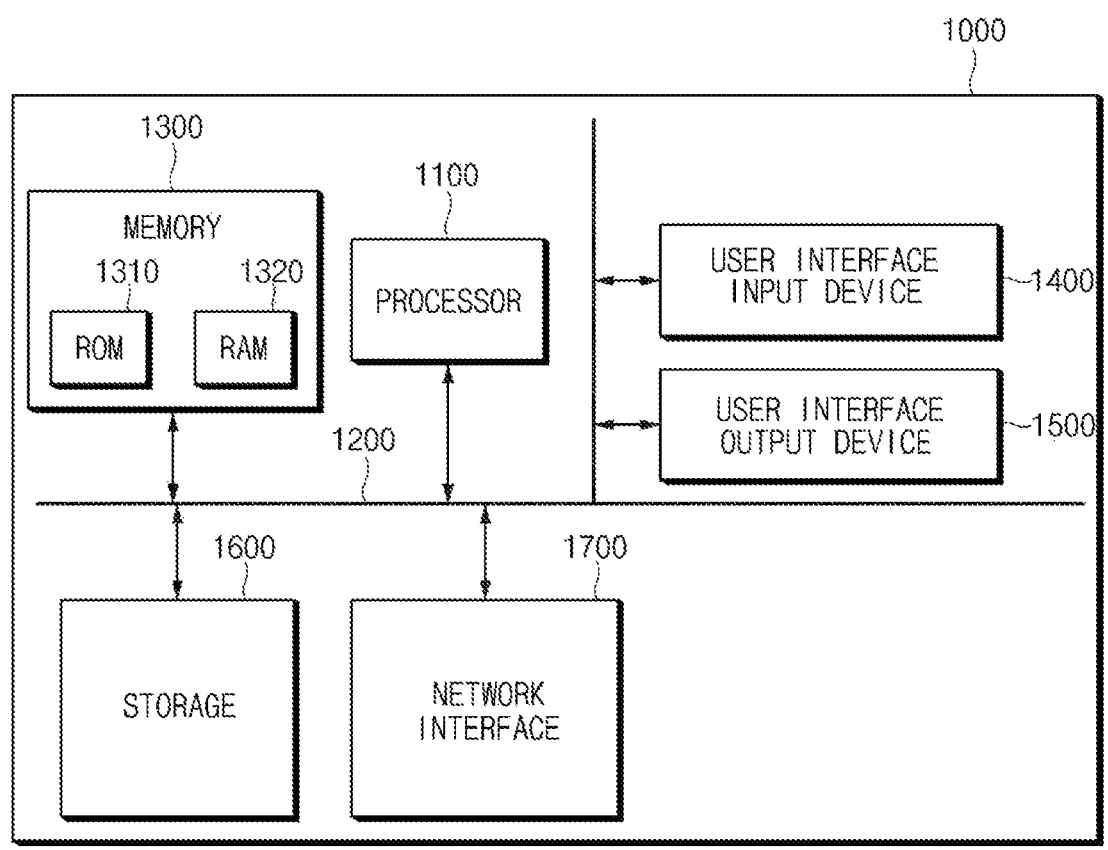
FIG. 7 is a block diagram illustrating a computing system according to an exemplary embodiment of the present disclosure.

FIG. 7 is a block diagram illustrating a computing system according to an exemplary embodiment of the present disclosure.

Referring to FIG. 7, a computing system 1000 may include at least one processor 1100, a memory 1300, a user interface input device 1400, a user interface output device 1500, storage 1600, and a network interface 1700, which are connected with each other via a bus 1200.

The processor 1100 may be a central processing unit (CPU) or a semiconductor device that processes instructions stored in the memory 1300 and/or the storage 1600. The memory 1300 and the storage 1600 may include various types of volatile or non-volatile storage media. For example, the memory 1300 may include a ROM (Read Only Memory) 1310 and a RAM (Random Access Memory) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM memory, a flash memory, a ROM, an EPROM, an EEPROM, a register, a hard disk, a removable disk, and a CD-ROM.

The exemplary storage medium may be coupled to the processor 1100, and the processor 1100 may read information out of the storage medium and may record information in the storage medium. Alternatively, the storage medium may be integrated with the processor 1100. The processor 1100 and the storage medium may reside in an application specific integrated circuit (ASIC). The ASIC may reside within a user terminal. In another case, the processor 1100 and the storage medium may reside in the user terminal as separate components.

The present technology may early and accurately detect drowsy driving of the user based on slow eye movement and an interval where there is no change in steering torque by a vehicle signal, thus preventing an accident due to the drowsy driving.

In addition, various effects directly or indirectly ascertained through the present disclosure may be provided.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the exemplary embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims, and all the technical ideas within the scope equivalent to the claims should be included in the scope of the present disclosure.

What is claimed is:

1. A drowsy driving management device, comprising:
    a processor configured to:
        determine whether slow eye movement of a user occurs and whether there is no change in steering torque, and
        determine that the user drives while drowsy when the slow eye movement of the user occurs and when there is no change in the steering torque for a predetermined period of time; and
    a storage storing information indicating whether the slow eye movement occurs and a result of determining whether there is no change in the steering torque,
    wherein the processor is configured to:
        calculate first eye movement information with respect to a vehicle based on information about a fixation of the user and information about a head pose of the user based on image data, and
        calculate second eye movement information with respect to an external environment based on the first eye movement information,
    wherein the information about the fixation includes a gaze yaw angle and a gaze pitch angle, and
    wherein the information about the head pose includes a head pose yaw angle and a head pose pitch angle.

2. The drowsy driving management device of claim 1, wherein the processor is configured to determine that the driver drives while drowsy, when there is no user maneuver in a state where the slow eye movement of the user occurs and where there is no change in the steering torque for the predetermined period of time.

3. The drowsy driving management device of claim 1, wherein the processor is configured to:
    calculate a first eye movement yaw angle with respect to the vehicle in the first eye movement information by subtracting the head pose yaw angle from the gaze yaw angle, and
    calculate a first eye movement pitch angle with respect to the vehicle in the first eye movement information by subtracting the head pose pitch angle from the gaze pitch angle.

4. The drowsy driving management device of claim 3, wherein the processor is configured to:
    calculate a second eye movement yaw angle with respect to the external environment in the second eye movement information using the first eye movement yaw angle and a vehicle yaw rate, and
    calculate a second eye movement pitch angle with respect to the external environment in the second eye movement information using the first eye movement pitch angle and a vehicle pitch angle.

5. The drowsy driving management device of claim 4, wherein the processor is configured to:

calculate an eye movement distance during the predetermined period of time using a value obtained by adding the second eye movement yaw angle and the second eye movement pitch angle, and determine that the slow eye movement occurs, when the eye movement distance is less than a predetermined reference value.

6. The drowsy driving management device of claim 1, wherein the processor is configured to determine that there is no change in the steering torque, when an output value of a steering torque sensor is less than a predetermined reference value.

7. A vehicle system, comprising:
a drowsy driving management device configured to:
determine whether slow eye movement of a user occurs and whether there is no change in steering torque, and
determine that the user drives while drowsy when the slow eye movement of the user occurs and when there is no change in the steering torque for a predetermined period of time; and
a warning device configured to output a warning to the user, when it is determined that the user drives while drowsy,
wherein the drowsy driving management device is configured to:
calculate first eye movement information with respect to a vehicle based on information about a fixation of the user and information about a head pose of the user based on image data, and
calculate second eye movement information with respect to an external environment based on the first eye movement information,
wherein the information about the fixation includes a gaze yaw angle and a gaze pitch angle, and
wherein the information about the head pose includes a head pose yaw angle and a head pose pitch angle.

8. The vehicle system of claim 7, wherein the warning device is configured to provide at least one or more of a visual warning, a tactile warning, and an audible warning.

9. The vehicle system of claim 7, further comprising:
a camera configured to detect information about a gaze of the user and information about a head pose of the user;
a yaw pitch sensor configured to sense a vehicle yaw rate and a vehicle pitch angle;
a steering torque sensor configured to sense a change in steering torque of the vehicle; and
a decelerator/accelerator pedal sensor configured to sense a change value in decelerator/accelerator pedal.

10. The vehicle system of claim 7, wherein the drowsy driving management device includes:
a processor configured to:
determine whether the slow eye movement of the user occurs and whether there is no change in the steering torque, and
determine that the user drives while drowsy when the slow eye movement of the user occurs and when there is no change in the steering torque for the predetermined period of time; and
a storage storing information indicating whether the slow eye movement occurs and a result of determining whether there is no change in the steering torque, the information and the result being obtained by the processor.

11. The vehicle system of claim 10, wherein the processor is configured to determine that the driver drives while drowsy, when there is no user maneuver in a state where the slow eye movement of the user occurs and where there is no change in the steering torque for the predetermined period of time.

12. A drowsy driving management method, comprising:
determining whether slow eye movement of a user occurs and whether there is no change in steering torque; and
determining that the user drives while drowsy, when the slow eye movement of the user occurs and when there is no change in the steering torque for a predetermined period of time,
wherein the determining whether slow eye movement of a user occurs and whether there is no change in steering torque includes:
calculating first eye movement information with respect to a vehicle based on information about a fixation of the user and information about a head pose of the user based on image data; and
calculating second eye movement information with respect to an external environment based on the first eye movement information,
wherein the information about the fixation includes a gaze yaw angle and a gaze pitch angle, and
wherein the information about the head pose includes a head pose yaw angle and a head pose pitch angle.

13. The drowsy driving management method of claim 12, wherein the determining that the user drives while drowsy includes determining that the driver drives while drowsy, when there is no user maneuver in a state where the slow eye movement of the user occurs and where there is no change in the steering torque for the predetermined period of time.

14. The drowsy driving management method of claim 12, wherein the determining whether slow eye movement of a user occurs and whether there is no change in steering torque includes:
calculating a first eye movement yaw angle with respect to the vehicle in the first eye movement information by subtracting the head pose yaw angle from the gaze yaw angle; and
calculating a first eye movement pitch angle with respect to the vehicle in the first eye movement information by subtracting the head pose pitch angle from the gaze pitch angle.

15. The drowsy driving management method of claim 14, wherein the determining whether slow eye movement of a user occurs and whether there is no change in steering torque includes:
calculating a second eye movement yaw angle with respect to the external environment in the second eye movement information using the first eye movement yaw angle and a vehicle yaw rate; and
calculating a second eye movement pitch angle with respect to the external environment in the second eye movement information using the first eye movement pitch angle and a vehicle pitch angle.

16. The drowsy driving management method of claim 15, wherein the determining whether slow eye movement of a user occurs and whether there is no change in steering torque includes:
calculating an eye movement distance during the predetermined period of time using a value obtained by adding the second eye movement yaw angle and the second eye movement pitch angle; and
determining that the slow eye movement occurs, when the eye movement distance is less than a predetermined reference value.

* * * * *